United States Patent
Verbiscar

(10) Patent No.: US 6,703,052 B2
(45) Date of Patent: Mar. 9, 2004

(54) LONG CHAIN MONOUNSATURATED ALCOHOL MIXTURES

(76) Inventor: Anthony J. Verbiscar, 160 E. Montecito Ave., Sierra Madre, CA (US) 91024

( * ) Notice: Subject to any disclaimer, the term of this patent is extended or adjusted under 35 U.S.C. 154(b) by 0 days.

(21) Appl. No.: 09/788,763

(22) Filed: Feb. 21, 2001

(65) Prior Publication Data

US 2001/0053800 A1 Dec. 20, 2001

Related U.S. Application Data

(62) Division of application No. 09/320,700, filed on May 26, 1999, now abandoned.
(60) Provisional application No. 60/087,406, filed on Jun. 1, 1998.

(51) Int. Cl.[7] .................. A61K 35/12; A01N 65/00; A01N 31/00; A01N 25/00
(52) U.S. Cl. .................. 424/725; 514/724; 514/783; 424/524
(58) Field of Search ................ 514/724, 783; 424/725, 524

(56) References Cited

U.S. PATENT DOCUMENTS 4,256,889 A * 3/1981 Shepard et al. ............... 546/63
4,404,283 A * 9/1983 Neidelman et al. ......... 435/134

OTHER PUBLICATIONS

Molaison et al., J. Amer. Oil Chem. Soc., 36:379–82, 1959.*
Taguchi, Proc. Sixth Int. Conf. Jojoba and Its Uses, eds. Wisniak and Zabicki, Ben–Gurian Univ. Negev, Beer–Shiva, Israel, 371–391, 1984.*

* cited by examiner

Primary Examiner—Michael Meller
(74) Attorney, Agent, or Firm—Foley & Lardner; Stephen E. Reiter

(57) ABSTRACT

A mixture of monounsaturated alcohols with 14 to 24 linear carbons in the linear chain is represented by jojoba alcohol, which remains an oily liquid at moderate ambient temperature. Jojoba alcohol is prepared by chemical hydrogenolysis of jojoba oil using a metal hydride reducing agent. A similar mixture of long chain monounsaturated alcohols can be prepared by hydrogenolysis of sperm whale oil. Mixtures of long chain monounsaturated alcohols penetrate epidermal layers of the skin to the vascular cells underneath where herpes viral infection, pain and other disorders occur.

5 Claims, No Drawings

LONG CHAIN MONOUNSATURATED ALCOHOL MIXTURES

RELATED U.S. APPLICATION

This application is a divisional application of the following parent application:
Parent Patent Pending Title: Topical Transdermal Treatments
Ser. No. 09/320,700
Filing Date: May 26, 1999, now abandoned, which claims benefit of provisional application Ser. 60/087,406 filed Jun. 1, 1998.
Applicant: Anthony J. Verbiscar

FIELD OF INVENTION

This invention relates to methods for the preparation of mixtures of long chain monounsaturated alcohols, such as jojoba alcohol. This oily liquid and its compositions are used for the topical treatment of subdermal infections such as herpes virus infections, and the transdermal delivery of pharmacological agents for the treatment of various disorders.

BACKGROUND OF INVENTION

A large percentage of the world population are infected with herpes viruses. Three of the most common herpes viruses are herpes simplex virus-1 (HSV-1) which is the cause of facial and ocular sores, herpes simplex virus-2 (HSV-2) which has a predilection for genital areas, and herpes simplex virus-3 (HSV-3), also named herpes zoster or varicella zoster, which causes chicken pox and later shingles. Once an individual is infected, herpes viruses become latent principally in nerve cells, and can reactivate to cause recurrences of the original symptoms. Herpes migration to the brain or spinal cord leads to encephalitis and meningitis, which are life-threatening conditions. Human herpes virus-8 (HHV-8) is associated with the skin cancer *Kaposi sarcoma*. These herpes episodes are each susceptible to topical treatments because the viruses replicate in subdermal cells during a recurrence, and before an eruption into a lesion. There are several treatment options for herpes infections but no cures. Several of the nucleoside analog drugs can be effective if taken prophylactically on a daily basis. They are less effective if administered at the time of the recurrence, either orally or topically. The nucleoside drugs inhibit viral replication by penetrating into the cell and interfering with nucleic acid production. They are not virucidal, and depend on a functional immune system to deactivate any virus present. New anti herpes virus agents, their targets and therapeutic potential have been reviewed (Alrabiah and Sacks, Drugs, 52: 17–32, 1996), as have topical treatments of herpes simplex virus infections (Hamuy and Berman, Europ. J. Dermatol., 8:310–319, 1998; Evans and Tyring, Dermatol. Clinic, 16: 409–419, 1998; Syed et al., Clin. Drug Invest., 16: 187–191, 1998).

Alcohols with chain lengths of 16 to 20 carbon atoms and 1 to 4 double bonds inhibited herpes simplex and another lipid enveloped viral bacteriophage in cell cultures (Sands et al., Antimicrob. Agents Chemother., 15: 67–73, 1979). These unsaturated alcohols were more potent in vitro than saturated alcohols with shorter chain lengths (Snipes et al., Antimicrob. Agents Chemother., 11: 98–104, 1977). A patent (Rivici et al., U.S. Pat. No. 4,513,008, 1985) describes the inhibition of enveloped viruses such as herpes with linear polyunsaturated acids, aldehydes or primary alcohols with chain lengths of 20 to 24 carbons and 5 to 7 double bonds. These reports were followed by the investigations and development of n-docosanol as a topical treatment for herpes infections n-Docosanol, also named 1-docosanol or behenyl alcohol, is a straight chain 22 carbon saturated alcohol, which occurs in the bark, flowers and fruit of the tree *Pygeum africanum*. n-Docosanol is reported to have broad spectrum in vitro activity against lipid enveloped viruses such as herpes (Katz)et al., Proc. Nat. Acad. Sci., 88:10825–10829, 1991; Katz et al., Ann. N.Y.Acad. Sci., 724: 472–488, 1994; Pope et al., J. Lipid Res., 37: 2167–2178, 1996; Pope et al., Antiviral Res., 40:85–94, 1998), and also the human inmmunodeficiency virus HIV (Marcelletti et al., AIDS Research and Human Retroviruses, 12: 71–74, 1996). These studies demonstrated that the antiviral activity of n-docosanol includes inhibition of fusion with or viral entry into the cell, while being mediated by intracellular metabolic biotransformation of the drug. A series of patents on the composition of mixtures of n-docosanol in formulations that render it useful for topical application supports these published reports (Katz, U.S. Pat. No. 4,874,794, 1989; Katz, U.S. Pat. No. 5,071,879, 1991; Katz, U.S. Pat. No. 5,166,219, 1992; Katz, U.S. Pat. No. 5,194,451, 1993; Katz, U.S. Pat. No. 5,534,554, 1996). n-Docosanol is not virucidal but is virustatic, interfereing with viral replication, and dependent on a functional immune system to destroy viruses. n-Docosanol is a crystalline waxy solid insoluble in water which needs to be formulated with a surfactant and carrier to facilitate dermal penetration and interaction at the target cell level, This limitation was also noted where several other virustatic long chain compounds with 18 plus linear carbons including amides, alkanes, acids and alcohols needed to be formulated with a surfactant and carrier to facilitate penetration of the epidermis (Katz et al., U.S. Pat. No. 5,534,554, 1996; Katz et al., PCT WO098/11887, 1998). The latter two reports claim a composition of n-docosanol or other long chain compounds with a surfactant and a pharmaceutically acceptable diluent or carrier as the active viral replication inhibitor, rather than the pure individual compounds. The preparation of n-docosanol is not reported in these patents. The long chain alcohols and other compounds are generally waxy solids, and would not be expected to penetrate skin layers alone without a carrier. In a study using 10% n-docosanol suspended in an aqueous system containing a non-ionic surfactant and a carrier, mean healing time of lesions in humans infected with herpes labialis (HSV-1) was shortened (Habbema et al., Acta Derm. Venereol., 76: 479–481, 1996). A 12% n-docosanol cream was tested as a possible transmision prophylactic of simian immunodeffi-ciency virus (SIV) in rhesus macque monkeys (Miller et al., Antiviral Res., 26: A277, 1995). Intravaginal application before exposure prevented transmission in five of the six animals tested. n-Docosanol and other saturated alcohols with chain lengths of 20 to 26 carbons reportedly promote corneal healing due to eye injury (Muller, U.S. Pat. No. 5,214,071, 1993; Muller, U.S. Pat. No. 5,296,514, 1994).

Jojoba oil has been available commercially for more than twenty years, and several million pounds are used in cosmetic formulations annually. Jojoba oil is a mixture of esters composed principally of both long chain mono unsaturated alcohols and carboxylic acids (Wisniak, The Chemistry and Technology of Jojoba Oil, publ. by American Oil Chemists Society, Champaign, Ill., 272 pp, 1987). A significant characteristic of jojoba oil is its ability to be absorbed quickly by the skin. Extensive testing and use of jojoba oil has established that it is completely non-toxic when applied to human sin, or administered orally to mice, rats, marmots and rabbits (Taguchi and Kunimoto, Cosmetics and Toiletries, 92: 53–61, 1977; Clark and Yermanos, Biochem. Biophys. Res. Commun., 102: 1409, 1981; Hamm, J. Food Sci., 49: 417–428, 1984; Verschuren and Nugteren, Food Chem. Toxicol., 27: 45–48, 1989). Humans who have ingested jojoba seeds, which are 50% oil, have not been harmed, although some nausea occurred when as much as 200 grams were eaten. In mice, jojoba oil has functioned as an intestinal lubricant (Verbiscar et al., J.Agric. Food Chem., 28: 571–578, 1980). It is estimated that about 20% of jojoba oil is split by esterases in the gastrointestinal system, thus producing jojoba alcohol in situ. After dermal absorption, jojoba oil would be at least partially metabolized to jojoba alcohol. Jojoba oil is a generally recognized as safe for cosmetic uses (Final Report on the Safety Assessment of Jojoba Oil and Jojoba Wax, J. Amer. Coll. Toxicol., 11(1): 57–74, 1992).

Jojoba alcohol has been prepared from jojoba oil by hydrogenolysis with sodium and alcohol (Molaison et al, J. Amer. Oil Chem. Soc., 36: 379–382, 1959). In this reaction, the carboxylic acid part of the ester is converted to its corresponding alcohol, in comparison with chemical hydrolysis where the fatty acids remain intact and must be separated from the alcohols in the mixture. Hydrogenolysis doubles the amount of jojoba alcohol that can be obtained from jojoba oil. One jojoba alcohol product prepared by hydrogenolysis resulted in a mixture of 6% octadec-9-enol, 62% eiocos-11-enol, 28% docos-13-enol and 4% tetracos-15-enol (Taguchi, Proc. Sixth Int. Conf. Jojoba and Its Uses, eds. Wisniak and Zabicki, Ben-Gurian Univ. Negev, Beer-Shiva, Israel, p 371–391, 1984). The actual alcohol composition will vary according to the source of jojoba oil. The relative amounts of individual alcohol components in jojoba alcohol depend on the ester composition of jojoba oil, a product obtained from seeds of the desert shrub *Simmonsia chinensis* harvested in the Southwestern United States, Mexico, Israel and South America.

Pure long straight chain monounsaturated alcohols are sometimes waxy liquid or low melting solids, but when in a mixture as in jojoba alcohol exist as a colorles odorless oil at normal ambient temperatures. A characteristic of jojoba alcohol is that it is readily absorbed by human skin, much like the parent jojoba oil. Jojoba alcohol does not require a carrier or surfactant to facilitate transdermal penetration. Jojoba alcohol is reported in one patent on lipstick components along with a large number and variety of other compounds with diverse structures and functions seeking lipocolor properties which would make the compositions feel less dry (Sato, Lipocolor Composition, U.S. 5,700,453, 1997). Jojoba alcohol is mentioned in the specifications of one patent on kojic acid where it is an excipient (Honda, U.S. Pat. No. 5,750,563, 1998).

The safety of jojoba alcohol for cosmetic uses has been reported (Taguchi, Proc. Sixth Int. Conf. Jojoba and Its Uses, eds. Wisniak and Zabicki, Ben-Gurian Univ. Negev, Israel, p 371–391, 1984). Mouse, rabbit, marmot and human tests were made for jojoba alcohol confirming that this product is very safe for topical application. Mutagenicity tests were also negative.

When applied to an incipient herpes simplex virus recurrence, jojoba alcohol quickly penetrates the epidermal layer to the subdermal cells where viral replication leading to symptomatic disease would otherwise occur (Verbiscar, PCT WO 9916245, Dec. 9, 1999, patents pending). Jojoba alcohol appears to function in the same manner that n-docosanol functions, that is by inhibiting lipid enveloped viruses from fusion with and entering into cells. Irritation is relieved and viral replication is delayed, while the host immune system is alerted to destroy the free virus units.

When treated early in the prodrome or even the erythema inflammation stages, herpes blisters do not form or at least are inhibited in persons with functional immune systems. This inhibitory action is applicable to enveloped viruses which cause lesions at epidermal surfaces. Herpes simplex viruses which cause recurrent facial sores (HSV-1) and genital sores (HSV-2), shingles (HSV-3) and Kaposi sarcoma (HHV-8) are treatment targets.

SUMMARY OF INVENTION

The metal hydride process for producing jojoba alcohol (II) from jojoba oil (I) is an improvement over the reported sodium hydrogenolysis because yields are higher and the reaction is safer and easier to carry out. The key product prepared is a mixture described as monounsaturated alcohols containing 14 to 24 carbon atoms represented in the reaction:

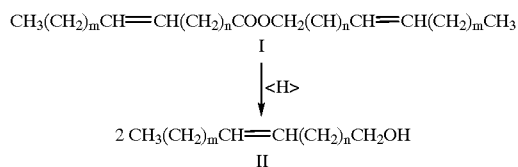

where m and n are 5 to 13, and the carbon—carbon double bonds are cis or trans. Jojoba alcohol is representitive of this general formula (II). The actual individual alcohol composition in the mixture can vary, as does the composition of esters in jojoba oil from which jojoba alcohol is derived. It is a characteristic of secondary plant metabolites such as the parent jojoba oil to vary in composition according to plant variety, pollination, soil and climate conditions of cultivation. Jojoba alcohol remains an oil at ambient temperatures above about 13 degrees centigrade because it is a mixture of monounsaturated alcohols. The melting point, or freezing point, is lowered by virtue of this being a mixture as is the melting point of any chemical compound which contains an impurity. Jojoba alcohol is not a single pure compound, and its freezing point behaves accordingly, maintaining it as an oil at ambient temperatures which are well below normal skin temperatures. This oily characteristic facilitates its applications and uses as a topical transdermal treatment product, without the need for a cofactor carrier or surfactant. The fact that jojoba alcohol is a mixture of individual pure compounds, and thus remains an oil at normal temperatures is significant to its functions. Mixtures of similar long chain monounsaturated alcohols can be prepared by hydrogenolysis of sperm whale oil, which is itself a mixture of mono esters of long chain monounsaturated carboxylic acids and long chain monounsaturared alcohols similar to jojoba oil. It is understood that mixtures of monounsaturated alcohols can be prepared by combining pure compounds similar to those in jojoba alcohol, and that these formulated mixtures will be oils and have properties similar to natural jojoba alcohol.

DETAILED DESCRIPTION OF INVENTION

In the previously reported sodium hydrogenolysis, a coreagent alcohol and the jojoba oil ester are added to liquid sodium in boiling toluene. The system generates nacent hydrogen which reduces the ester groups to alcohol groups without reducing the carbon—carbon double bonds. In our hands, this process yielded a 73% yield of pure distilled jojoba alcohol. However, workup and purification of the final product was difficult due to the presence of carboxylic acid by-products resulting from partial hydrolysis of the ester rather rather than hydrogenolysis. The sodium salts of these long chain fatty acids act as surfactants and cannot be water-washed out of the mixture. In addition, while this reaction can be done readily in small quantities, large scale production with liquid sodium presents difficulties. To circumvent these problems, we invented a new chemical hydrogenolysis of the ester group of jojoba oil to the alcohols using a commercial reagent named sodium bis-(2-methoxyethoxy)aluminum hydride (Bazant et al., Tetrahedron Letters, 29; 3303-3306, 1968). With this reagent, a 90.5% yield of jojoba alcohol was obtained which is identical to the liquid sodium hydrogenolysis product, but with no dangerous reactants or workup problems. This jojoba alcohol freezing point was about 13 degrees centigrade, and remains an oil at normal ambient temperatures. Major alcohol components of jojoba alcohol are octadec-9-enol, eicos-11-enol, docos-13-enol and tetracos-15-enol. The actual amount of any individual alcohol in a jojoba alcohol preparation will vary according to the source of jojoba oil used in the hydrogenolysis. Other alcohols, ranging in chain length from 14–24 carbon atoms, may also be present as minor components (Wisniak, Chemistry and Technology of Jojoba Oil, publ. American Oil Chemists Society, Champaign, Ill., 272 pp, 1987). This process is also applicable to sperm whale oil, producing a similar mixture of long chain monounsaturated alcohols. Although the sodium bis(2-methoxyethoxy)aluminum hydride is available commercially, it can be prepared in situ for direct hydrogenolysis of jojoba oil. A convenient preparation reacts one mole of sodium plus one mole of aluminum with two moles of 2-methoxyethanol in benzene or toluene at temperatures above 100° C. under hydrogen pressure (J. Vit, B. Cosensky and J. Machacek, French patent, 1,515,582). The disappearance of the insoluble sodium and aluminum metals indicates this reaction is complete and the reagent is formed. Jojoba oil can then be added slowly to the reagent solution, at low temperatures to complete the hydrogenolysis to jojoba alcohol. Workup of the final product is the same as for the metal hydride system described here.

The generic structure of the major components of this jojoba alcohol mixture and examples of individual mono unsaturated alcohols composing jojoba alcohol follows, where the double bond can exist in cis and trans forms and m and n can vary from 5 to 13 carbons.

| | $CH_3(CH_2)_mCH=CH(CH_2)_nCH_2OH$ | |
|---|---|---|
| | m | n |
| Hexadec-7-enol | 7 | 5 |
| Octadec-7-enol | 9 | 5 |
| Octadec-9-enol | 7 | 7 |
| Eicos-11-enol | 7 | 9 |
| Docos-13-enol | 7 | 11 |
| Tetracos-15-enol | 7 | 13 |

Jojoba alcohol is a mixture of principally monounsaturated linear alcohols with 14 to 24 carbon atoms in the chain. A mixture of these alcohols is readily prepared by hydrogenolysis of jojoba oil, which is a mixture of esters. Mixtures of monounsaturated linear alcohols can also be prepared from other sources. Sperm whale oil is an example of mixtures of long chain esters of monounsaturated alcohols and carboxylic acids which can also be converted to the corresponding mixture of long chain monounsaturated alcohols using this metal hydride hydrogenolysis process. A mixture of the individual alcohol components can also be prepared by combining specific amounts of each alcohol. The more alcohols in the mixture, the more likely will the mixture be liquid at ambient temperatures. A formulated mixture of individual alcohols will act like jojoba alcohol as a transdermal penetration carrier and viral fusion inhibitor. Jojoba alcohol represents mixtures of these alcohols which will remain liquified at ambient temperatures, thus facilitating its use in topical transdermal treatments. While the specifications contain particular details, these should not be construed as limitations of the scope of the invention, but rather examples of preferred embodiments. Jojoba alcohol can actually be comprised of any percent variation of the individual long chain monounsaturated alcohols, depending on the source of the jojoba oil from which it is derived. There are many varieties of *Simmonsia chinensis* from which the jojoba oil is obtained from the seed, with different pollination source plants, and different cultural conditions. All of these differences contribute to the final chemical composition of the jojoba oil esters. The most significant structural factors in the jojoba alcohol compounds is that they are highly lipophylic with a hydrophylic hydroxyl end group, and a carbon carbon double bond in the inner chain which facilitates transdermal penetration.

EXAMPLE 1

Jojoba Alcohol by Sodium and Alcohol Hydrogenolysis

The ester group of jojoba oil was reduced to jojoba alcohol by the sodium and alcohol procedure reported previously (Molaison et al., J. Amer. Oil Chem. Soc., 36: 379–382,1959) with minor variations. A suspension of 20.2 grams (0.88 moles) of sodium in 100 ml of dry toluene was stirred well and brought to reflux, whereupon the sodium liquified. A solution of 120 grams (0.2 moles) of purified jojoba oil and 36.5 grams (0.48 moles) of 2-methoxyethanol in 100 ml of dry toluene was added slowly with vigorous stirring under reflux. The reaction solution became clear yellow with a small amount of suspended solids. After additional stirring and refluxing, the solution was allowed to cool as a waxy solid formed. Water, 100 ml, was added slowly with stirring as some foaming occurred. The emulsified toluene phase was separated from the emulsified aqueous phase, then washed with 100 ml of saline. The toluene was removed by distillation and hexane was added to the residue. A white waxy solid, 14 grams, was collected and identified by an infrared spectrum as the sodium salt of some of the carboxylic acid portion of the jojoba oil. Vacuum distillation of the hexane soluble fraction yielded 88.2 grams (73%) of a clear colorless oil. An infrared spectrum was consistant with the known structure. The residue in the distillation pot contained unreacted ester and more hydrolytic carboxylic acid, as determined by an IR spectrum.

EXAMPLE 2

Jojoba Alcohol by Sodium Bis(2-methoxyethoxy) aluminumhydride Hydrogenolysis A 70 ml (0.245 moles) portion of a 3.5 M soln. of sodium bis(2-methoxyethoxy)aluminum hydride reagent (Bazant et al., Tetrahedron Letters, 29: 3303–3306, 1968) was charged into a reaction flask with 30 ml of dry toluene. A solution of 120 grams (0.2 moles) of jojoba oil in 120 ml of toluene was dried over molecular sieves. This solution was added dropwise over 30 minutes to the well stirred reducing reagent as frothing occurred After the addition, the reaction solution was warmed for an hour and a sample was taken. An infrared spectrum showed the absence of ester carbonyl absorption indicating that the hydrogenolysis was complete. After a total of two hours warming, 60 ml of water was added dropwise causing an initial frothing, then the formation of a gelatinous precipitate. The supernatant toluene solution was decanted and the precipitate was washed well with hexane. The combined toluene-hexane extract was dried over calcium sulfate. The clear, colorless, oily jojoba alcohol distilled at 188-218°/15 mm, and weighed 108.6 grams (90.5%). It solidified in the refrigerator at about 13° C. An infrared spectrum of this product was identical with the sodium reduction product, and was consistent with its structure as follows for wavelength $cm^{-1}$, group, type; 3340, OH, strong broad stretch; 3000, $CH_3$, sharp weak stretch; 2920, $CH_2$, strong sharp stretch; 2850, CH, medium sharp stretch; 1650, C=C, weak broad stretch; 1455, $CH_2$, strong deformation; 1375, C—$CH_3$, weak deformation; 1050, C—O, strong stretch; 715, $(CH_2)_n$, strong skelatal. An infrared spectrum of jojoba oil starting material shows no hydroxyl absorption but a strong sharp ester carbonyl peak at 1735 $cm^{-1}$ along with a carbon carbon double bond at 1650 $cm^{-1}$, with a carbon hydrogen stretch and deformation pattern similar to jojoba alcohol.

What is claimed is:

1. A method for the preparation of a mixture of principally monounsatured alcohols containing 14–24 carbon atoms, represented by the formula:

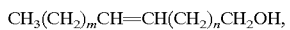

$$CH_3(CH_2)_mCH=CH(CH_2)_nCH_2OH,$$

wherein m and n are each independently 5–13, and the carbon—carbon double bonds are cis or trans, by the chemical reduction of a mixture of principally monounsaurated esters selected from the group consisting of jojoba oil and sperm whale oil, said method comprising contacting said mixture of principally monounsaturated esters with an effective amount of a complex metal hydride reducing agent.

2. The method of claim 1 wherein said complex metal hydride reducing agent is sodium bis(2-methoxyethoxy) aluminum hydride.

3. The method of claim 1 wherein said mixture of principally monounsaturated esters is jojoba oil.

4. The method of claim 1 wherein said mixture of principally monounsaturated esters is sperm whale oil.

5. The method of claim 1 wherein said mixture of principally monounsaturated alcohols comprises octadec-9-enol, eicos-11-enol, docos-13-enol, and tatracos-15-enol.

* * * * *